US009997041B2

(12) United States Patent
Sabota

(10) Patent No.: US 9,997,041 B2
(45) Date of Patent: *Jun. 12, 2018

(54) NON-CONTACT ALARM VOLUME REDUCTION

(71) Applicant: Segars California Partners, LP, Austin, TX (US)

(72) Inventor: Peter Sabota, Austin, TX (US)

(73) Assignee: Segars California Partners, LP, Austin, TX (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/677,655

(22) Filed: Aug. 15, 2017

(65) Prior Publication Data

US 2017/0345271 A1    Nov. 30, 2017

Related U.S. Application Data

(63) Continuation of application No. 15/281,754, filed on Sep. 30, 2016, now Pat. No. 9,767,666, which is a continuation of application No. 14/214,821, filed on Mar. 15, 2014, now Pat. No. 9,483,917.

(60) Provisional application No. 61/788,387, filed on Mar. 15, 2013.

(51) Int. Cl.
| | | |
|---|---|---|
| G08B 23/00 | (2006.01) | |
| G08B 21/02 | (2006.01) | |
| G08B 5/36 | (2006.01) | |
| G08B 3/10 | (2006.01) | |
| A61B 5/00 | (2006.01) | |
| A61G 11/00 | (2006.01) | |

(52) U.S. Cl.
CPC .............. *G08B 21/02* (2013.01); *A61B 5/742* (2013.01); *A61G 11/00* (2013.01); *G08B 3/10* (2013.01); *G08B 5/36* (2013.01); *A61G 2203/10* (2013.01)

(58) Field of Classification Search
CPC . G08B 21/02; G08B 5/36; G08B 3/10; G08B 21/22; A61G 11/00; A61G 2203/30; A61G 7/002; A61B 5/742; A61B 5/746; A61B 5/1113; A61B 5/002; A61B 5/7405; G06F 19/3418
USPC .......................... 340/573.1, 541, 506, 286.07
See application file for complete search history.

(56) References Cited

U.S. PATENT DOCUMENTS

| | | |
|---|---|---|
| 3,675,051 A | 7/1972 | Mioduski |
| 4,951,032 A | 8/1990 | Langsam |
| 5,031,258 A | 7/1991 | Shaw |
| 5,086,526 A | 2/1992 | Van Marcke |
| 5,372,545 A | 12/1994 | Noda et al. |
| 5,382,791 A | 1/1995 | Leff et al. |
| 5,772,291 A | 6/1998 | Byrd et al. |
| 5,817,003 A | 10/1998 | Moll et al. |

(Continued)

FOREIGN PATENT DOCUMENTS

| | | |
|---|---|---|
| EP | 0872227 A2 | 10/1998 |
| JP | 0210028 | 12/1990 |
| JP | 08103437 | 4/1996 |

OTHER PUBLICATIONS

GE Healthcare, Panda Warmers for Labor & Delivery, 2007, 7 pages.

*Primary Examiner* — Anh V La
(74) *Attorney, Agent, or Firm* — Barnes & Thornburg LLP

(57) ABSTRACT

A method and apparatus for providing a caregiver the capability of modifying the tone and volume of an audible alarm for a medical device based on non-contact methods.

1 Claim, 2 Drawing Sheets

(56) References Cited

U.S. PATENT DOCUMENTS

| | | |
|---|---|---|
| 5,912,624 A | 6/1999 | Howard, II |
| 5,952,835 A | 9/1999 | Coveley |
| 5,954,225 A | 9/1999 | Powe |
| 6,007,553 A | 12/1999 | Hellenkamp et al. |
| 6,161,655 A | 12/2000 | Lejon et al. |
| 6,249,706 B1 | 6/2001 | Sobota et al. |
| 6,296,606 B1 | 10/2001 | Goldberg et al. |
| 6,334,069 B1 | 12/2001 | George et al. |
| 6,350,228 B1 | 2/2002 | Richards et al. |
| 6,443,885 B1 | 9/2002 | Schuler |
| 6,733,437 B2 | 5/2004 | MacKin |
| 6,876,303 B2 | 4/2005 | Reeder et al. |
| 9,483,917 B2 * | 11/2016 | Sabota .................... G08B 3/10 |
| 2002/0082498 A1 | 6/2002 | Wendt et al. |
| 2003/0079744 A1 | 5/2003 | Bonney et al. |
| 2005/0046549 A1 | 3/2005 | Hoyle |
| 2009/0261979 A1 | 10/2009 | Breed |
| 2010/0127866 A1 * | 5/2010 | Klein .................... A61B 5/1113 |
| | | 340/541 |
| 2010/0131280 A1 | 5/2010 | Bogineni |
| 2011/0001605 A1 * | 1/2011 | Kiani .................... G06F 19/327 |
| | | 340/5.6 |
| 2013/0290001 A1 | 10/2013 | Yun |

\* cited by examiner

NON-CONTACT ALARM VOLUME REDUCTION

CROSS-REFERENCE TO RELATED APPLICATIONS

This application claims priority to U.S. patent application Ser. No. 15/281,754, filed Sep. 30, 2016, which claimed priority to U.S. patent application Ser. No. 14/214,821, now U.S. Pat. No. 9,483,917, filed Mar. 15, 2014, which claimed the benefit of U.S. Provisional application 61/788,387, filed Mar. 15, 2013, all of which are incorporated herein by reference.

BACKGROUND

This disclosure relates to the field of various patient care devices used in the care of critical patients. Example devices could be infant warming devices, anesthesia machines, infusion pumps, ventilators, or neonatal intensive care units. In many of these situations the situation can be one in which the care provider is required to operate in sterile conditions and is wearing sterile gloves. Such patient care devices often have alarm condition sensors that monitor certain parameters and determine when an alarm condition exists. This alarm condition may be associated with the patient or with the patient care device itself. These alarms are important to patient safety in that the caregivers must respond to satisfy the alarm condition or the alarm continues to function and alert the user. The alarms are often initially rather loud to ensure the caregiver hears them but can then be distracting as the caregiver responds to the problem indicated by the alarm. Most methods in the market require silencing of the alarm through physical contact with the user interface which can be a concern for the caregiver if a procedure is occurring in a sterile environment and they do not want to touch a non-sterile interface.

One solution in the market is to turn off the alarm through a non-contact method. This is described in U.S. Pat. No. 6,733,437 to Mackin. But by turning off the alarm in this manner there is a risk that the alarm condition gets forgotten and not corrected, that the alarm gets erroneously turned off without the users knowledge, or that the user walks away after the procedure and forgets that the alarm is still silenced which could have patient safety ramifications.

What is needed is an alternate approach, one that reduces the nuisance level of the alarm but continues to alert the caregiver so that the alarm condition is not potentially forgotten as in other approaches.

The example that will be used for purposes of this disclosure is an infant warming device that is used to provide heat support to premature infants who cannot sustain their own body temperature. In the treatment of infants, and particularly those born prematurely, it is necessary to provide heat to the infant during the care and treatment of the infant and to minimize heat loss from the infant's body. An apparatus for providing such heat will be referred to in this disclosure as an infant warming device. In general such an apparatus comprises a flat planar surface on which the infant rests while various procedures are carried out. There are normally protective guards that surround the infant and some type of overhead heater directing radiant energy toward the infant. It should be understood that these infant warming devices might have other descriptive names, such as, for example, an infant care device, or an infant warming center, an infant incubator, or combination type device, and this disclosure anticipates any of those other names.

Although an infant warming device is being used here for illustrative purposes this disclosure anticipates that numerous other patient care devices, such as the aforementioned anesthesia machines, infusion pumps, ventilators, or neonatal intensive care units can make use of this approach.

BRIEF SUMMARY

The described need is met with a non-contact method of reducing the volume of the alarm to a pre-set user level and duration. The medical device would incorporate a method of non-contact sensing using any number of technologies (proximity, optical, thermal, ultrasonic, capacitance etc.) and after sensing, the device would lower the volume to a user pre-defined level and time. Additionally the user would have the option of changing the tone or frequency of the audible alarm in addition to changing the absolute volume. The user interface could also be changed under this condition by modifying the color of the alarm or the alarm message or icon as it is displayed on the screen to give a visual indication to the user that the alarm level or tone has been changed.

The need is met by a non-contact alarm volume reduction system used in a patient care apparatus including at least a sensor or event detection mechanism for monitoring the condition of the patient or of the patient care apparatus; an alarm processing circuit operating off of the sensor or event detection mechanism that sends a signal to an audible alarm sounding device to produce a sound or visual display; a non-hand contact volume reduction sensor operated by human intervention that signals the alarm processing circuit to operate at a predefined tone and volume for a pre-set time; wherein the non-contact volume sensor is activated without hand contact by a human.

DETAILED DESCRIPTION

Figure 1:
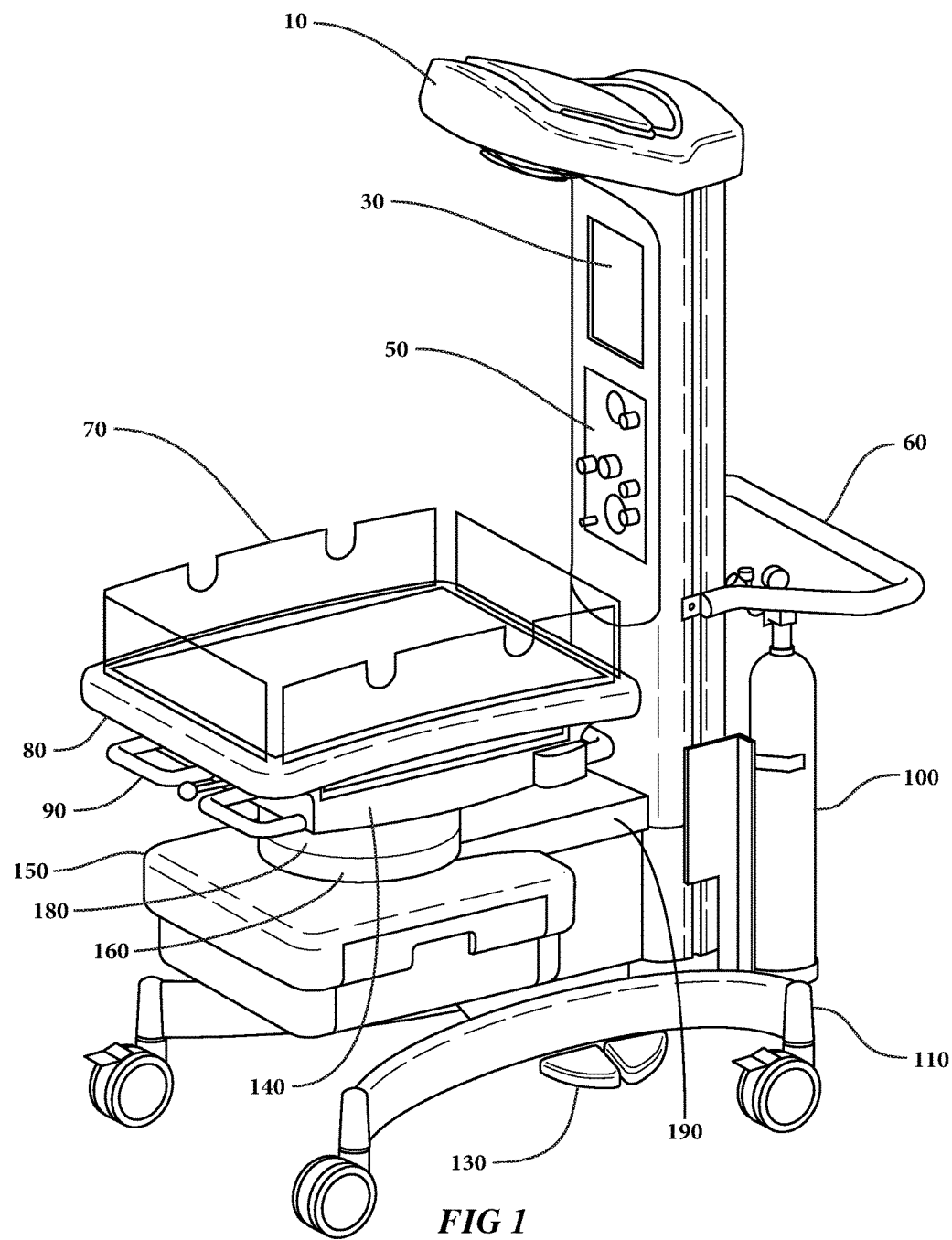
FIG. 1 is a view of an infant care center that can include the inventive concept to be described in this disclosure.

Referring now to FIG. 1 is an illustrative infant warming center that can include the inventive concept to be described in this disclosure. The center includes an infant bed 80 that underlies an infant positioned thereon. The infant bed has a surrounding sidewall 70 and rides upon a patient support mechanism 140. The patient bed and surrounding sidewalls may enclose a heated mattress. A vertical column structure mounted on the infant warming center supports a radiant heater head 10, containing a radiant heater 170 (FIG. 3). The radiant heater assembly is designed to optimize the heat focused on the infant. The vertical column structure may have a user interface 30 and a resuscitation module 50. The infant warming device's main computer controller may reside in the vertical column structure or may reside in the patient support mechanism. Handles 60, 90, are used to move the infant warming device around as it can be moved on flat surfaces via legs 110 with attached wheels and controlled with footswitches 130. On the rear side of the column is a location for carrying a remote gas supply tank 100. Under the patient support mechanism 140 is a cantilever cover 160 and turret cover 180 for shrouding the rotation mechanisms, with a cantilever arm 190 that supports the patient support, vertical column, and supports a storage enclosure 150.

Figure 2:
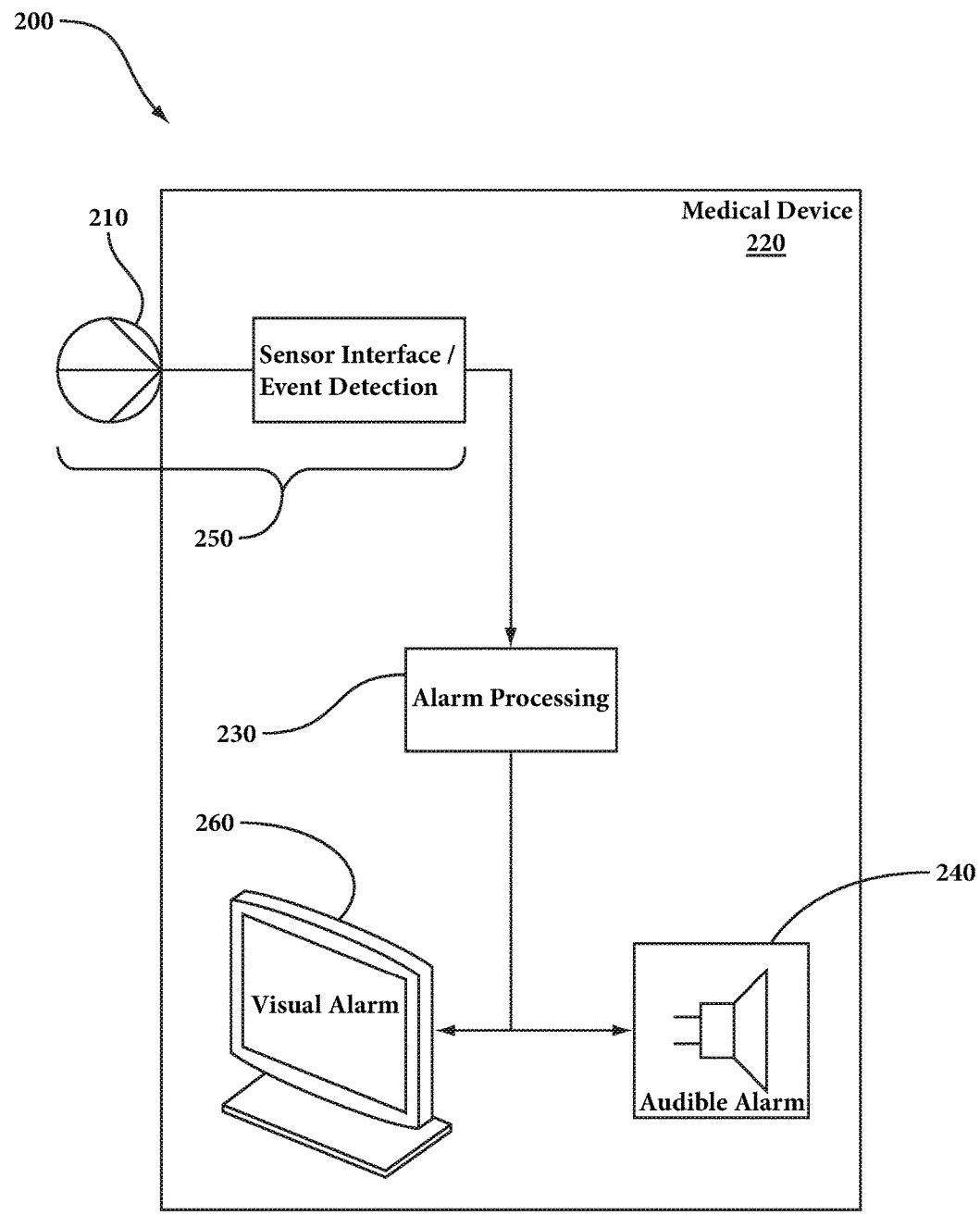
FIG. 2 is a schematic view of the proposed non-contact alarm reduction system.

FIG. 2, shown generally by the numeral 200, illustrates a total system comprising a patient care system (medical device 220) with an integral alarm processing circuit 230 and embedded software that includes an audible alarm 240 and a visual alarm 260. A sensor interface/event detection system 250 can monitor both the condition of the patient and key parameters of the infant care apparatus and inputs that information to alarm processing 230. The system receives feedback from the user (via, hand, foot, etc.) and signals the alarm circuit to change the standard alarm to a new alarm with a predefined tone and volume level for a pre-set time. Transducer input 210 represents a variety of possible non-contact technologies (proximity, optical, thermal, ultrasonic, capacitance etc.), all of which are possible and are all anticipated in this disclosure.

In one embodiment the non-contact alarm volume reduction system used in a patient care apparatus could be activated by optical sensing to detect an object in proximity to patient care apparatus.

In another embodiment the non-contact alarm volume reduction system used in a patient care apparatus could be activated by temperature sensing to detect an object in close proximity to patient care apparatus.

In another embodiment the non-contact alarm volume reduction system used in a patient care apparatus could be activated by an air motion sensor adapted to a change in air pressure.

In another embodiment the non-contact alarm volume reduction system used in a patient care apparatus could be activated by a sound recognition system responsive to the voice of a person.

In another embodiment the non-contact alarm volume reduction system used in a patient care apparatus could be activated by contact with foot of a caregiver.

In another embodiment the non-contact alarm volume reduction system used in a patient care apparatus could be activated by an ultrasonic sensor.

In another embodiment the non-contact alarm volume reduction system used in a patient care apparatus could be activated by a capacitance sensor.

In another aspect the non-contact alarm volume reduction system used in a patient care apparatus is programmable and adjustable by the user.

In another aspect the non-contact alarm volume reduction system used in a patient care apparatus the level, tone or frequency of the reduced alarm volume system can be programmed.

In another aspect the non-contact volume reduction system can be pre-programmed by the user to pre-set the reduced volume and the alternate tone of the audible alarm, as well as the time interval for the alarm.

Advantages Over the Prior Art

The advantage of the proposed system is that it is a non-contact method for addressing alarm noises in the clinical workspace but unlike other systems does not completely silence the alarm. This allows the user to not be distracted by a high alarm volume but the alarm would continue to signal at a reduce level or a different tone. This concept does not have the risk of completely turning off the alarm.

Although certain embodiments and their advantages have been described herein in detail, it should be understood that various changes, substitutions and alterations could be made without departing from the coverage as defined by the appended claims. Moreover, the potential applications of the disclosed techniques is not intended to be limited to the particular embodiments of the processes, machines, manufactures, means, methods and steps described herein. As a person of ordinary skill in the art will readily appreciate from this disclosure, other processes, machines, manufactures, means, methods, or steps, presently existing or later to be developed that perform substantially the same function or achieve substantially the same result as the corresponding embodiments described herein may be utilized. Accordingly, the appended claims are intended to include within their scope such processes, machines, manufactures, means, methods or steps.

The invention claimed is:

1. A patient care apparatus comprising:
an alarm system, comprising:
an event detection sensor for monitoring the condition of the patient care apparatus;
an audible alarm sounding device operable to produce audible sounds;
a non-contact volume reduction sensor configured to generate a signal in response to detecting a caregiver, the non-contact volume reduction sensor being an optical sensor that is configured to detect the caregiver in proximity to the patient care apparatus;
a user interface operable to display visual information about the alarm system; and
an alarm processing circuit configured to (i) receive signals from the event detection sensor and the non-contact volume reduction sensor, (ii) generate a first control signal based on the signals from the event detection sensor, and (iii) generate a second control signal when the signal is received from the non-contact volume reduction sensor,
wherein the audible alarm sounding device is operable to (i) produce an audible sound at a first predefined volume in response to receiving the first control signal from the alarm processing circuit and (ii) reduce the audible sound from the first predefined volume to a second predefined volume in response to receiving the second control signal from the alarm processing circuit, the second predefined volume being different from the first predefined volume.

* * * * *